(12) United States Patent
Ward et al.

(10) Patent No.: US 11,123,466 B2
(45) Date of Patent: *Sep. 21, 2021

(54) METHODS FOR REMOVING CYTOKINES FROM BLOOD WITH SURFACE IMMOBILIZED POLYSACCHARIDES

(71) Applicant: EXTHERA MEDICAL CORPORATION, Martinez, CA (US)

(72) Inventors: Robert S. Ward, Orinda, CA (US); Keith R. McCrea, Concord, CA (US); Olle Larm, Bromma (SE); Lars Adolfsson, Uppsala (SE)

(73) Assignee: ExThera Medical Corporation, Martinez, CA (US)

( * ) Notice: Subject to any disclaimer, the term of this patent is extended or adjusted under 35 U.S.C. 154(b) by 524 days.

This patent is subject to a terminal disclaimer.

(21) Appl. No.: 16/113,904

(22) Filed: Aug. 27, 2018

(65) Prior Publication Data

US 2018/0361050 A1 Dec. 20, 2018

Related U.S. Application Data

(60) Continuation of application No. 15/199,737, filed on Jun. 30, 2016, now Pat. No. 10,086,126, which is a
(Continued)

(51) Int. Cl.
*A61M 1/36* (2006.01)
*A61K 31/60* (2006.01)
(Continued)

(52) U.S. Cl.
CPC ............. *A61M 1/362* (2014.02); *A61K 31/60* (2013.01); *A61K 31/722* (2013.01);
(Continued)

(58) Field of Classification Search
CPC .................. A61M 1/38; A61M 1/3679; A61M 2202/0057; A61M 1/362; A61M 1/3496; A61K 31/727

See application file for complete search history.

(56) References Cited

U.S. PATENT DOCUMENTS 3,782,382 A 1/1974 Naftulin et al.
4,103,685 A 8/1978 Lupien et al.
(Continued)

FOREIGN PATENT DOCUMENTS

CN 1395620 A 2/2003
CN 101370536 A 2/2009
(Continued)

OTHER PUBLICATIONS

Abdul-Razzak, K. et al., "Fetal and newborn calf thymus as a source of chromatin proteins: Purification of HMG-1 and HMG-2," Preparative Biochemistry and Biotechnology, 17(1):51-61, 1987.
(Continued)

*Primary Examiner* — Adam Marcetich
(74) *Attorney, Agent, or Firm* — Kilpatrick Townsend & Stockton LLP

(57) ABSTRACT

The present invention is directed to a method for removing cytokines and/or pathogens from blood or blood serum (blood) by contacting the blood with a solid, essentially non microporous substrate which has been surface treated with heparin, heparan sulfate and/or other molecules or chemical groups (the adsorbent media or media) having a binding affinity for the cytokine or pathogen(s) to be removed (the adsorbates), and wherein the size of the interstitial channels within said media is balanced with the amount of media surface area and the surface concentration of binding sites
(Continued)

on the media in order to provide adequate adsorptive capacity while also allowing relatively high flow rates of blood through the adsorbent media.

20 Claims, 2 Drawing Sheets

Related U.S. Application Data continuation of application No. 14/261,390, filed on Apr. 24, 2014, now Pat. No. 9,408,962, which is a division of application No. 12/958,355, filed on Dec. 1, 2010, now Pat. No. 8,758,286.

(60) Provisional application No. 61/265,675, filed on Dec. 1, 2009.

(51) Int. Cl.
  *A61K 31/722* (2006.01)
  *A61K 31/727* (2006.01)
  *A61K 31/728* (2006.01)
  *A61M 1/34* (2006.01)
  *A61M 1/38* (2006.01)

(52) U.S. Cl.
  CPC .......... *A61K 31/727* (2013.01); *A61K 31/728* (2013.01); *A61M 1/3472* (2013.01); *A61M 1/3486* (2014.02); *A61M 1/3496* (2013.01); *A61M 1/36* (2013.01); *A61M 1/3621* (2013.01); *A61M 1/3673* (2014.02); *A61M 1/3679* (2013.01); *A61M 1/3687* (2013.01); *A61M 1/38* (2013.01); *A61M 2202/0057* (2013.01)

(56) References Cited

U.S. PATENT DOCUMENTS

| | | |
|---|---|---|
| 4,415,665 A | 11/1983 | Mosbach et al. |
| 4,430,496 A | 2/1984 | Abbott |
| 4,613,665 A | 9/1986 | Larm |
| 4,637,994 A | 1/1987 | Tani et al. |
| 4,643,896 A * | 2/1987 | Asakura .............. C07K 14/445 424/268.1 |
| 4,820,302 A | 4/1989 | Woodroof |
| 4,955,870 A | 9/1990 | Ridderheim et al. |
| 5,116,962 A | 5/1992 | Stuber et al. |
| 5,211,850 A | 5/1993 | Shettigar et al. |
| 5,403,917 A | 4/1995 | Boos et al. |
| 5,437,861 A | 8/1995 | Okarma et al. |
| 5,447,859 A | 9/1995 | Prussak |
| 5,476,509 A | 12/1995 | Keogh, Jr. et al. |
| 5,753,227 A | 5/1998 | Strahilevitz |
| 6,037,458 A | 3/2000 | Hirai et al. |
| 6,159,377 A | 12/2000 | Davankov et al. |
| 6,197,568 B1 | 3/2001 | Marks et al. |
| 6,248,127 B1 | 6/2001 | Shah et al. |
| 6,312,907 B1 | 11/2001 | Guo et al. |
| 6,461,665 B1 | 10/2002 | Scholander |
| 6,544,727 B1 | 4/2003 | Hei |
| 6,559,290 B1 | 5/2003 | Nakatani et al. |
| 6,653,457 B1 | 11/2003 | Larm et al. |
| 7,179,660 B1 | 2/2007 | Kirakossian |
| 7,408,045 B2 | 8/2008 | Maruyama et al. |
| 7,695,609 B2 | 4/2010 | Soundarrajan et al. |
| 8,273,357 B2 * | 9/2012 | Hacohen .............. A61K 47/61 424/193.1 |
| 8,663,148 B2 | 3/2014 | Larm et al. |
| 8,758,286 B2 | 6/2014 | Ward et al. |
| 9,173,989 B2 | 11/2015 | Larm et al. |
| 9,408,962 B2 | 8/2016 | Ward et al. |
| 9,669,150 B2 | 6/2017 | Larm et al. |
| 9,764,077 B2 | 9/2017 | Larm et al. |
| 10,086,126 B2 | 10/2018 | Ward et al. |
| 10,188,783 B2 | 1/2019 | Larm et al. |
| 10,457,974 B2 | 10/2019 | Ward et al. |
| 10,487,350 B2 | 11/2019 | Ward et al. |
| 10,537,280 B2 | 1/2020 | McCrea et al. |
| 10,639,413 B2 | 5/2020 | McCrea et al. |
| 10,688,239 B2 | 6/2020 | Larm et al. |
| 10,857,283 B2 | 12/2020 | Ward et al. |
| 2001/0005487 A1 | 6/2001 | Kamibayashi et al. |
| 2002/0018985 A1 | 2/2002 | Eibl et al. |
| 2002/0040012 A1 * | 4/2002 | Johannes Stiekema ..................... A61P 43/00 514/54 |
| 2002/0058032 A1 | 5/2002 | Hirai et al. |
| 2002/0068183 A1 | 6/2002 | Huang et al. |
| 2002/0197249 A1 | 12/2002 | Brady et al. |
| 2002/0197252 A1 | 12/2002 | Brady et al. |
| 2003/0021780 A1 | 1/2003 | Smith et al. |
| 2003/0044769 A1 | 3/2003 | Ogino et al. |
| 2003/0148017 A1 | 8/2003 | Tuominen et al. |
| 2004/0084358 A1 | 5/2004 | O'Mahony et al. |
| 2004/0115278 A1 | 6/2004 | Putz et al. |
| 2004/0140265 A1 | 7/2004 | Lihme |
| 2004/0176672 A1 | 9/2004 | Silver et al. |
| 2004/0182783 A1 | 9/2004 | Walker et al. |
| 2004/0185553 A9 | 9/2004 | Hei |
| 2004/0202783 A1 | 10/2004 | Baumann et al. |
| 2005/0098500 A1 | 5/2005 | Collins et al. |
| 2005/0142542 A1 | 6/2005 | Hei et al. |
| 2005/0244371 A1 | 11/2005 | Lentz |
| 2005/0271653 A1 | 12/2005 | Strahilevitz |
| 2006/0030027 A1 * | 2/2006 | Ellson ..................... A61M 1/38 435/287.1 |
| 2006/0093999 A1 | 5/2006 | Hei |
| 2006/0252054 A1 | 11/2006 | Ping |
| 2007/0190050 A1 | 8/2007 | Davidner et al. |
| 2007/0218514 A1 | 9/2007 | Smith et al. |
| 2007/0231217 A1 | 10/2007 | Clinton et al. |
| 2008/0021365 A1 | 1/2008 | Kobayashi et al. |
| 2008/0138434 A1 | 6/2008 | Brady et al. |
| 2008/0268464 A1 | 10/2008 | Schumacher et al. |
| 2008/0314817 A1 | 12/2008 | Fujita et al. |
| 2009/0105194 A1 | 4/2009 | Flengsrud et al. |
| 2009/0136586 A1 | 5/2009 | Larm et al. |
| 2009/0173685 A1 | 7/2009 | Imai et al. |
| 2009/0186065 A1 * | 7/2009 | Tillman ................ A61B 5/153 424/423 |
| 2009/0206038 A1 | 8/2009 | Thomas |
| 2009/0246800 A1 | 10/2009 | Mattingly et al. |
| 2009/0325276 A1 | 12/2009 | Battrell |
| 2010/0021622 A1 | 1/2010 | Meng et al. |
| 2010/0040546 A1 | 2/2010 | Hyde et al. |
| 2010/0069816 A1 | 3/2010 | Brady et al. |
| 2010/0079360 A1 | 4/2010 | McLaughlin et al. |
| 2010/0098666 A1 | 4/2010 | Wright |
| 2010/0112725 A1 | 5/2010 | Babu et al. |
| 2010/0145317 A1 | 6/2010 | Laster et al. |
| 2010/0216226 A1 | 8/2010 | Hyde et al. |
| 2010/0217173 A1 | 8/2010 | Hyde et al. |
| 2010/0239673 A1 | 9/2010 | Linhardt |
| 2010/0249689 A1 | 9/2010 | Larm et al. |
| 2010/0276359 A1 | 11/2010 | Ippommatsu et al. |
| 2010/0291588 A1 | 11/2010 | McDevitt |
| 2010/0326916 A1 | 12/2010 | Wrazel et al. |
| 2011/0150911 A1 | 6/2011 | Choo |
| 2011/0171713 A1 | 7/2011 | Bluchel et al. |
| 2011/0184377 A1 | 7/2011 | Ward et al. |
| 2011/0224645 A1 | 9/2011 | Winqvist et al. |
| 2012/0040429 A1 | 2/2012 | Federspiel et al. |
| 2012/0219561 A1 | 8/2012 | Alt et al. |
| 2012/0305482 A1 | 12/2012 | McCrea et al. |
| 2013/0102948 A1 | 4/2013 | Reich et al. |
| 2013/0131423 A1 | 5/2013 | Wang et al. |
| 2014/0012097 A1 | 1/2014 | McCrea et al. |
| 2014/0131276 A1 | 5/2014 | Larm et al. |
| 2014/0231357 A1 | 8/2014 | Ward et al. |
| 2015/0111849 A1 | 4/2015 | McCrea et al. |
| 2015/0260715 A1 | 9/2015 | Hu et al. |
| 2016/0022898 A1 | 1/2016 | Larm et al. |

(56) References Cited

U.S. PATENT DOCUMENTS

| | | |
|---|---|---|
| 2016/0082177 A1 | 3/2016 | Ward et al. |
| 2016/0084835 A1 | 3/2016 | Ward et al. |
| 2016/0101229 A1 | 4/2016 | McCrea et al. |
| 2016/0214935 A1 | 7/2016 | Hutchinson et al. |
| 2016/0331886 A1 | 11/2016 | Ward et al. |
| 2017/0035956 A1 | 2/2017 | McCrea et al. |
| 2017/0073727 A1 | 3/2017 | Ward et al. |
| 2017/0340803 A1 | 11/2017 | Larm et al. |
| 2019/0038826 A1 | 2/2019 | McCrea et al. |
| 2019/0143027 A1 | 5/2019 | Larm et al. |
| 2020/0023001 A1 | 1/2020 | Ebong et al. |
| 2020/0056221 A1 | 2/2020 | Ward et al. |
| 2020/0171233 A1 | 6/2020 | Mccrea et al. |
| 2020/0297913 A1 | 9/2020 | Larm et al. |
| 2020/0338256 A1 | 10/2020 | Ward et al. |

FOREIGN PATENT DOCUMENTS

| | | |
|---|---|---|
| CN | 101784294 A | 7/2010 |
| CN | 102740859 A | 10/2012 |
| CN | 102791307 | 11/2012 |
| CN | 106255520 A | 12/2016 |
| DE | 4217917 A1 | 12/1993 |
| EP | 0306617 A | 3/1989 |
| EP | 0321703 A | 6/1989 |
| EP | 0533946 A1 | 3/1993 |
| EP | 0616845 A | 9/1994 |
| EP | 0810027 A | 12/1997 |
| EP | 1044696 A2 | 10/2000 |
| EP | 1057529 A | 12/2000 |
| EP | 1110602 A | 6/2001 |
| EP | 1219639 A | 7/2002 |
| EP | 2087916 A1 | 8/2009 |
| EP | 2556849 A1 | 2/2013 |
| GB | 217812 A | 10/1986 |
| JP | 54-127493 U | 9/1979 |
| JP | 58-053757 A | 3/1983 |
| JP | 58-146354 A | 8/1983 |
| JP | 4-89500 A | 3/1992 |
| JP | 6040926 A | 2/1994 |
| JP | 6-505248 A | 6/1994 |
| JP | 7-178161 A | 7/1995 |
| JP | 96-510166 A | 10/1996 |
| JP | 11-502703 A | 3/1999 |
| JP | 2000-086688 A | 3/2000 |
| JP | 2000-217575 A | 8/2000 |
| JP | 2000-515543 A | 11/2000 |
| JP | 2001-190273 A | 7/2001 |
| JP | 2002-505101 A | 2/2002 |
| JP | 2002-509518 A | 3/2002 |
| JP | 2003-128502 A | 5/2003 |
| JP | 2003-520048 A | 7/2003 |
| JP | 2005-514127 A | 5/2005 |
| JP | 2005-519744 A | 7/2005 |
| JP | 2005-532130 A | 10/2005 |
| JP | 2009-521413 A | 6/2009 |
| JP | 2010-518046 A | 5/2010 |
| JP | 2010-530288 A | 9/2010 |
| JP | 2011-509083 A | 3/2011 |
| JP | 2012-501708 A | 1/2012 |
| JP | 2013-512078 A | 4/2013 |
| JP | 2014-500735 A | 1/2014 |
| JP | 2014-523914 A | 9/2014 |
| KR | 10-2008-0077405 A | 8/2008 |
| WO | 91-04086 A | 4/1991 |
| WO | 92/14361 A1 | 9/1992 |
| WO | 94/26399 A1 | 11/1994 |
| WO | 95/05400 | 2/1995 |
| WO | 96/29083 A1 | 9/1996 |
| WO | 96/40857 A1 | 12/1996 |
| WO | 97/35660 A1 | 10/1997 |
| WO | 98/05341 A1 | 2/1998 |
| WO | 98/29727 A2 | 7/1998 |
| WO | 99/0086 A1 | 2/1999 |
| WO | 99/45104 A3 | 11/1999 |
| WO | 00/23792 | 4/2000 |
| WO | 00/038763 | 7/2000 |
| WO | 00/66260 A | 11/2000 |
| WO | 01/18060 A | 3/2001 |
| WO | 01/53525 A2 | 7/2001 |
| WO | 02/060512 | 8/2002 |
| WO | 03/033143 A1 | 4/2003 |
| WO | 2003/057356 A2 | 7/2003 |
| WO | 2003/078023 A1 | 9/2003 |
| WO | 2004/008138 A2 | 1/2004 |
| WO | 2004/009798 A2 | 1/2004 |
| WO | 2005/021799 A2 | 3/2005 |
| WO | 2007/058592 A1 | 5/2007 |
| WO | 2007/069983 A1 | 6/2007 |
| WO | 2007/101064 A2 | 9/2007 |
| WO | 2007/146162 A2 | 12/2007 |
| WO | 2008/095905 A2 | 8/2008 |
| WO | 2008/157570 A2 | 12/2008 |
| WO | 2009/086343 A2 | 7/2009 |
| WO | 2010/029317 A2 | 3/2010 |
| WO | 2011/068897 A1 | 6/2011 |
| WO | 2011/100354 A1 | 8/2011 |
| WO | 2012/051595 A1 | 4/2012 |
| WO | 2012/112724 A1 | 8/2012 |
| WO | 2012/172341 A1 | 12/2012 |
| WO | 2013/012924 A2 | 1/2013 |
| WO | 2013/188073 A1 | 12/2013 |
| WO | 2014/209782 A1 | 12/2014 |
| WO | 2015/069942 A1 | 5/2015 |
| WO | 2015/164198 A1 | 10/2015 |

OTHER PUBLICATIONS

Alarabi, A. et al., "Treatment of pruritus in cholestatic jaundice by bilirubin- and bile acid-adsorbing resin column plasma perfusion," Scandinavian Journal of Gastroenterology, 27(3):223-6, 1992.

Alfaro et al., "Interleukin-8 in cancer pathogenesis, treatment and follow-up," Cancer Treat Rev., Nov. 2017, vol. 60:24-31 (abstract only).

Axelsson, J. et al., "Cytokines in blood from septic patients interact with surface-immobilized heparin," ASAIO Journal, 56:48-51, 2010.

Bhakdi, S. and Tranum-Jensen, J., "Alpha-toxin of *Staphylococcus aureus*," Microbiological Reviews, 55(4):733-751, 1991.

Bindslev et al., "Treatment of acute respiratory failure by extracorporeal carbon dioxide elimination performed with a surface heparinized artificial lung," Anesthesiology, 67(1):117-120, 1987.

Bjorklund et al., Abstract of "Synthesis of silica-based heparin-affinity adsorbents," J. Chrom. A., 728(1-2):149-169, 1996.

Celik, T. et al., "Treatment of lyme neuroborreliosis with plasmapheresis," J. Clinical Apheresis, 31:476-478, 2016.

Chase, H., "Affinity separations utilising immobilised monclonal antibodies—a new tool for the biochemical engineer," Chemical Engineering Science, 39(7-8):1099-1125, 1984.

Chen et al., "Microbial subversion of heparin sulfate proteoglycans," Mol. Cells, 26:415-426, 2008.

Dixon et al., "Anthrax," New England Journal of Medicine, 341(11):815-826, 1999.

Dubreuil et al., "Effect of heparin binding on Helicobacter pylori resistance to serum," J. Med. Micro., 53:9-12, 2004.

Francy, D. et al., "Comparison of filters for concentrating microbial indicators and pathogens in lake water samples," Applied and Environmental Microbiology, 79(4):1342-52, 2012.

Fujita, M. et al., "Adsorption of inflammatory cytokines using a heparin-coated extracorporeal circuit," Artificial Organs, 26(12:)1020-1025, 2002.

Garg, L. et al., "Isolation and separation of HMG proteins and histones H1 and H5 and core histones by column chromatography on phosphocellulose," Protein Expression and Purification, 14(2):155-159, 1998.

Haase et al., "The effect of three different miniaturized blood purification devices on plasma cytokine concentration in an ex vivo model of endotoxinemia," Int. J. Artif. Organs, 31(8):722-729, 2008.

(56) References Cited

OTHER PUBLICATIONS

Hirmo, S. et al., "Sialyglycoconjugate- and proteoglycan-binding microbial lectins," Institute of Medical Microbiology, University of Lund, (Online). Retrieved Oct. 19, 1997 (Retrieved on Mar. 16, 2004). Retrieved from the Internet: <URL: http//www.plab.ku.dk/tcbh/Lectins12/Hirmo/paper.htm>.
International Preliminary Report on Patentability, dated Aug. 21, 2013, PCT Application No. PCT/US2012/025316; 8 pages.
International Search Report; PCT/SE2006/001421 dated Mar. 30, 2007.
International Search Report; PCT/US2010/058596 dated Mar. 29, 2011.
International Search Report; PCT/US2011/024229 dated May 30, 2011.
International Search Report; PCT/US2012/025316 dated May 23, 2012.
International Search Report; PCT/US2013/042377 dated Sep. 9, 2013.
International Search Report; PCT/US2014/043358 dated Dec. 1, 2014.
International Search Report; PCT/US2014/064419 dated Feb. 12, 2015.
International Search Report; PCT/US2015/026340 dated Jul. 28, 2015.
International Search Report; PCT/US2015/051239 dated Dec. 17, 2015.
International Search Report; PCT/US2016/057121 dated Dec. 30, 2016.
International Search Report; PCT/US2017/058536; dated Jan. 17, 2018.
Kenig, M. et al., "Identification of the heparin-binding domain of TNF-alpha and its use for efficient TNF-alpha purification by heparin-Sepharose affinity chromatography," J. Chromatography B, 867:119-125, 2008.
Keuren et al., "Thrombogenecity of polysaccharide-coated surfaces," Biomaterials, 24:1917-24, 2003.
Kim et al., "Role of the heparin in regulating a transcapillary exchange in far north conditions," Bulletin of the Siberian Branch of the Russian Academy of Medical Sciences, 2(108), 2003.
Kishimoto, S. et al., "Human stem cell factor (SCF) is a heparin-binding cytokine," J. Biochem., 145(3):275-278, 2009.
Kumari, N. et al., "Role of interleukin-6 in cancer progression and therapeutic resistance," Tumour Biol., Sep. 2016, vol. 37(9), pp. 11553-11572 (abstract only).
Larm et al., "A new non-thrombogenic surface prepared by selective covalent binding of heparin via a modified reducing terminal residue," Biomater Med Devices Artif Organs, 11(2&3):161-173, 1983.
Lian, S. et al., "Elevated expression of growth-regulated oncogene-alpha in tumor and stromal cells predicts unfavorable prognosis in pancreatic cancer," Medicine, Jul. 2016, 95(30), pp. 1-8.
Lopatkin et al., "Efferent methods in medicine, M.," Medicine, pp. 266, 272-273, 276-279, 1989.
Low, R. et al., "Protein n, a primosomal DNA replication protein of *Escherichia coli*," Journal of Biological Chemistry, 257(11):6242-6250, 1982.
Mandal, "Sialic acid binding lectins," Experientia, 46:433-439, 1990.
Mariano et al., "Tailoring high-cut-off membranes and feasible application in sepsis-associated acute renal failure: in vivo studies," Nephrol Dial Transplant, 20:1116-1126, 2005.
Mattsby-Baltzer, I. et al,, "Affinity apheresis for treatment of bacteremia caused by *Staphylococcus aureus* and/or methicillin-resistant *S. aureus* (MRSA)," J. Microbiol. Biotechnol., 21(6):659-664, 2011.
Millen, H. et al., "Glass wool filters for concentrating waterborne viruses and agricultural zoonotic pathogens," J. Vis. Exp., 61:e3930, 2012.
Nadkarni et al., Abstract of "Directional immobilization of heparin onto beaded supports," Anal. Biochem., 222(1):59-67, 1994.
Ofek et al., "Mannose binding and epithelial cell adherence of *Escherichia coli*," Infection and Immunity, 22(1):247-254, 1978.
Park, P. et al., "Activation of Syndecan-1 ectodomain shedding by *Staphylococcus aureus* α-toxin and β-toxin," J. Biol. Chem., 279(1):251-258, 2004.
Popova et al., "Acceleration of epithelial cell syndecan-1 shedding by anthrax hemolytic virulence factors," BMC Microbiology, 6:8, pp. 1-6, 2006.
Rauvala, H. et al., "Isolation and some characteristics of an adhesive factor of brain that enhances neurite outgrowth in central neurons," Journal of Biological Chemistry, 262(34):16625-16635, 1987.
Rauvala, H. et al., "The adhesive and neurite-promoting molecule p30: Analysis of the amino-terminal sequence and production of antipeptide antibodies that detect p30 at the surface of neuroblastoma cells and of brain neurons," Journal of Cell Biology, 107(6,1):2293-2305, 1988.
Riesenfeld et al., "Quantitative analysis of N-sulfated, N-acetylated, and unsubstituted glucosamine amino groups in heparin and related polysaccharides," Anal Biochem, 188:383-389, 1990.
Sagnella et al., "Chitosan based surfactant polymers designed to improve blood compatibility on biomaterials," Colloids and Sufaces B: Biointerfaces, 42:147-155, 2005.
Salek-Ardakani, S. et al., "Heparin and heparan sulfate bind interleukin-10 and modulate its activity," Blood, 96:1879-1888, 2000.
Salmivirta, M. et al., "Neurite growth-promoting protein (Amphoterin, p30) binds syndecan," Experimental Cell Research, 200:444-451, 1992.
Sanchez, J. et al., "Control contact activation on end-point immobilized heparin: The role of antithrombin and the specific antithrombin-binding," J. Bio. Mat. Res., 29:665-661, 1995.
Sasaki et al., Abstract: "Improved method for the immbolization of heparin," J. Chrom., 400:123-32, 1987.
Sato, T. et al., "Experimental study of extracorporeal perfusion for septic shock," Asaio Journal, 39(3):M790-M793, 1993.
Schefold et al., "A novel selective extracorporeal intervention in sepsis: immunoadsorption of endotoxin, interluekin 6, and complement-activating product 5A," Shock, 28(4):418-425, 2007.
Sharon, "Bacterial lectins, cell-cell recognition and infectious disease," FEBS letters, 217(2):145-157, 1987.
Swartz, "Recognition and management of anthrax—an update," New Engl. J. Med., 345(22):1621-1626, 2001.
Thomas et al., "Common oligosaccharide moieties inhibit the adherence of typical and atypical respiratory pathogens," Journal of Microbiology, 53:833-840, 2004.
Utt, M. et al., "Identification of heparan sulphate binding surface proteins of Helicobacter pylori: inhibition of heparan sulphate binding with sulphated carbohydrate polymers," J. Med. Microbiol., 46:541-546, 1997.
Wang, H. et al., "HMG-1 as a late mediator of endotoxin lethality in mice," Science, 285:248-251, 1999.
Ward et al., "Specificity of adsorption in a prototype whole blood affinity therapy device for removal of *Staphylococcus aureus*," Society for Biomaterials 2013 Annual Meeting and Exposition, Apr. 10, 2013, p. 1.
Waugh D. and Wilson, C., "The interleukin-8 pathway in cancer," Clin. Cancer Res., 14(21):6735-41, 2008.
Webb, L. et al., "Binding to heparan sulfate or heparin enhances neutrophil responses to interleukin 8," PNAS USA, 90:7158-62, 1993.
Weber et al., "Development of specific adsorbents for human tumor necrosis factor-α: influence of antibody immobilization on performance and biocompatibility," Biomacromolecules, 6:1864-1870, 2005.
Weir, D., "Carbohydrates as recognition molecules in infection and immunity," FEMS Microbiology Immunology, 47:331-340, 1989.
Wendel et al., "Coating-techniques to improve the hemocompatibility of artificial devices used for extracorporeal circulation," European Journal of Cardio-thoracic Surgery, 16:342-350, 1999.
Yu, J. et al., "Adhesion of coagulase-negative staphylococci and adsorption of plasma proteins to heparinized polymer surfaces," Biomaterials, 15(10):805-814, 1994.
Zhou et al., Abstract: "Heparin-agarose aqueous ethanol suspension," J. Mol. Bio., 271(3):12, 1997.

(56) References Cited

OTHER PUBLICATIONS

Andrade-Gordon, P. et al., "Interaction of heparin with plasminogen activators and plasminogen: effects on the activation of plasminogen," Biochemistry, 25(14):4033-4040, 1986.

Andreasen, P. et al., "The plasminogen activation system in tumor growth, invasion, and metastasis," Cellular and Molecular Life Sciences, 57(1):25-40, 2000.

Ascencio, F. et al., "Affinity of the gastric pathogen Helicobacter pylori for the N-sulphated glycosaminoglycan heparan sulphate," J. Med. Microbiol., 38:240-244, 1993.

Bartlett, A. and P. Park, "Proteoglycans in host-pathogen interactions: molecular mechanisms and therapeutic implications," Expert Rev. Mol. Med., 12(e5):1-33, 2015.

Brat, D. et al., "The role of interleukin-8 and its receptors in gliomagenesis and tumoral angiogenesis," Neuro-oncology, 7(2):122-133, 2005.

Choong, P. et al., "Urokinase plasminogen activator system: a multifunctional role in tumor progression and metastasis," Clinical Orthopaedics and Related Research, 415(Suppl):S46-58, 2003.

Era, K. et al., "Development of Systems for Passive and Active CAVH," J. Japanese Society for Dialysis Therapy, 19(2):175-181, 1986.

Frick, I. et al., "Interactions between M proteins of *Streptococcus pyogenes* and glycosaminoglycans promote bacterial adhesion to host cells," Eur. J. Biochem, 270(10):2303-11, 2003.

GE Healthcare, "Size exclusion chromatography columns and resins, Selection guide," 2010, retrieved online at <<https://cdn.gelifesciences.com/dmm3bwsv3/AssetStream.aspx?mediaformatid=10061&destinationid=10016&assetid=13947>> on Jun. 27, 2019, 10 pages.

Ghannoum, M. et al., "Extracorporeal treatment for carbamazepine poisoning: Systematic review and recommendations from the EXTRIP workgroup," Clinical Toxicology, 52:993-1004, 2014.

Lemaire, M. et al., "Treatment of paediatric vancomycin intoxication: a case report and review of the literature," NDT Plus, 3:260-264, 2010.

Murphy, J. et al., "Structural and functional basis of CXCL 12 (stromal cell-derived factor-1 a) binding to heparin," Journal of Biological Chemistry, 282(13):10018-10027, 2007.

Office Action dated Jun. 23, 2020 in Japanese Patent Application No. 2017-515161, with English translation, retrieved from <https://globaldossier.uspto.gov/#/details/JP/2017515161/A/129021> on Aug. 13, 2020.

Sanaka, T. et al., "Continuous Arteriovenous Hemofiltration," Artificial Organs, 14(5):1822-1830, 1985.

Smorenburg, S. et al., "The complex effects of heparins on cancer progression and metastasis in experimental studies," Pharmacological Reviews, 53(1):93-106, 2001.

Tonnaer, E. et al., "Involvement of glycosaminoglycans in the attachment of pneumococci to nasopharyngeal epithelial cells," Microbes and Infection, 8:316-322, 2006, available online Sep. 16, 2005.

Wadstrom, T. and A. Ljungh, "Glycosaminoglycan-binding microbial proteins in tissue adhesion and invasion: key events in microbial pathogenicity," J. Med. Microbiol., 48(3):223-233, 1999.

\* cited by examiner

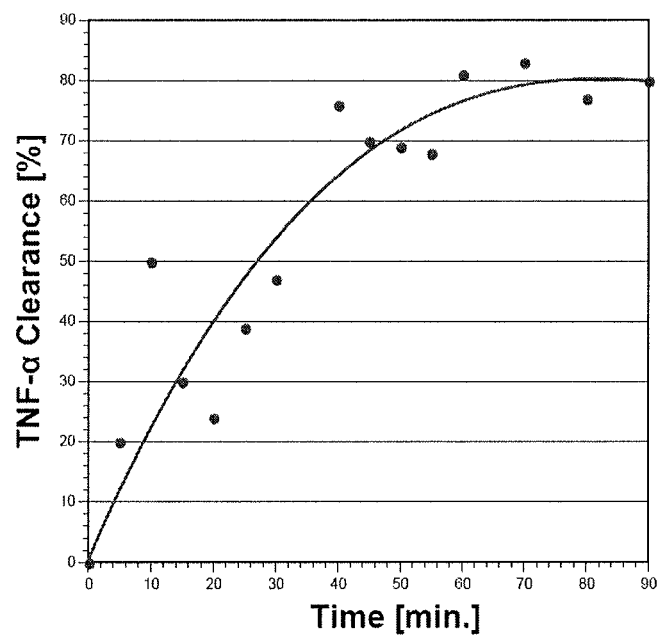
Figure 1: Removal of TNF-α from 5 L of Platelet Poor Plasma

QCM plot. Mass of heparin adsorbed

METHODS FOR REMOVING CYTOKINES FROM BLOOD WITH SURFACE IMMOBILIZED POLYSACCHARIDES

CROSS-REFERENCE TO RELATED APPLICATIONS

This application is a continuation of U.S. application Ser. No. 15/199,737, filed Jun. 30, 2016, allowed, which application is a continuation of U.S. application Ser. No. 14/261, 390, filed Apr. 24, 2014, now U.S. Pat. No. 9,408,962, which application is a divisional of U.S. application Ser. No. 12/958,355, filed Dec. 1, 2010, now U.S. Pat. No. 8,758,286, which application claims priority to U.S. Application No. 61/265,675, filed Dec. 1, 2009. The teachings all of which are hereby incorporated by reference in their entireties for all purposes.

FIELD OF THE INVENTION

The present invention is directed to a method for removing cytokines and/or pathogens from blood or blood serum (blood) by contacting the blood with a solid, essentially non microporous substrate which has been surface treated with a polysaccharide adsorbent, such as heparin, heparan sulfate and/or other molecules or chemical groups (the adsorbent media or media) having a binding affinity for the cytokine or pathogen(s) to be removed (the adsorbates), and wherein the size of the interstitial channels within said media is balanced with the amount of media surface area and the surface concentration of binding sites on the media in order to provide adequate adsorptive capacity while also allowing relatively high flow rates of blood through the adsorbent media. The result is that transport of adsorbates to the binding sites on the media occurs largely by forced convection. By (forced) convection is meant, for example, flow produced by a pressure gradient generated by a pump, by the application of external pressure to a flexible container (or internal pressure to a rigid container), by a gravity head/ elevation difference, or by the difference in arterial pressure and venous pressure in the patient being treated. The invention provides clinically-relevant adsorptive capacity within the range of safe flow rates typically used in clinical extracorporeal blood circuits, e.g., in dialysis, cardiopulmonary bypass, and extra corporeal membrane oxygenation of blood. The method is in direct contrast to the much slower diffusive transport of adsorbates typically required with porous adsorbent media, which require adsorbates to diffuse through a microporous membrane, and/or into microscopic pores before binding to adsorption sites on, behind, or within the media, and which therefore require very low flow rates to achieve significant separations during each passage of blood. The present invention also provides a method of treating a disease by removing cytokines and/or pathogens from blood by contacting blood with an essentially nonporous substrate coated with a polysaccharide adsorbent, such as heparin, heparan sulphate, and/or, other adsorbent materials, and a device for performing the method and treatment.

BACKGROUND OF THE INVENTION

A wide variety of disease conditions are characterized by the presence of elevated concentrations of cytokines and/or pathogens in the blood stream. Some such conditions are treated by therapies designed to kill the pathogen, e.g. through the administration of drugs, e.g., anti-infective pharmaceuticals. Some other conditions are treated by therapies that attempt to reduce the concentration of blood-borne cytokines or pathogens in the patient. Other diseases are treated by therapies that attempt to directly remove only specific components from the patient's blood.

For example, Guillian-Barre syndrome is currently understood to be an autoimmune disorder triggered by viral infection that stimulates the body's immune system to over produce antibodies or other proteins which can attack the patient's nervous system, causing increasing levels of paralysis. Most patients recover over time, though such patients appear to be susceptible to recurrence of the condition from subsequent viral infections. One method for treating Guillian-Barre syndrome involves plasmapheresis to 'clean' the patient's blood by removing antibodies believed to be attacking the patient's nervous system.

Certain biologically active carbohydrates and polysaccharides can remove harmful substances from blood and biological fluids.

Heparin is a polysaccharide that can be isolated from mammalian tissue. It has a very specific distribution in mammalian tissue; being present only in the basophilic granules of mast cells. Since its discovery in 1916 by the American scientist McLean, heparin has been recognized for its ability to prevent blood from clotting, and for its relatively short half-life in the body. Systemic heparin, administered by injection of the free drug, has been used clinically for more than 50 years as a safe and effective blood anticoagulant and antithrombotic agent. The effects of heparin on blood coagulation/clotting diminish fairly quickly after administration is halted, making its use during surgery and other procedures effective and safe. That is, heparin's anticoagulant and antithrombogenic properties are useful during many medical procedures, for example to minimize undesirable interactions between blood and the man-made surfaces of extracorporeal circuits. Once the procedure is over, the administration of heparin may then be terminated. The heparin concentration in the patient's blood diminishes to a safe level within a few hours because of its short half life in the body. This is particularly important following surgery when healing depends on the ability of blood to clot at the surgical site to avoid bleeding complications. In addition to its well established and continuing use in the treatment of thromboembolic disorders, and the prevention of surface-induced thrombogenesis, heparin has more recently been found to have a wide range of other functions apparently unrelated to its function as an anticoagulant. For example, a large number of proteins in blood are now known to bind with high affinity, to heparin and/or the closely-related polysaccharide heparan sulfate which is also found in animal tissue, including the blood-contacting luminal surface of healthy blood vessels (where it may contribute to preventing circulating blood from clotting on contact with the walls of the blood vessels). Some examples are antithrombin (AT), fibronectin, vitronectin, growth factors (e.g. the fibroblast growth factors, the insulin like growth factors, etc.). Human serum albumin (HSA) also binds to heparin, but with a lower affinity despite its high concentration in blood.

Others have considered utilizing the selective adsorption properties of systemic, free heparin for hindering infections, by introducing heparin fragments and/or so-called sialic-containing fragments directly into the vascular system. This therapy was based on the assumption that these fragments would bind to the lectins on the microbes and block them so they could not bind to the receptors on the mammalian cell surface. Although this approach has been investigated by many scientists, only limited success has been reported to date. The most common problem has been bleeding complications associated with the large amounts of free heparin introduced into the blood stream, e.g., by injection, to achieve a clinically-useful reduction of pathogenic microbes. The present invention does not require the use of any free, systemic heparin for efficacy, and thus may eliminate bleeding complications. This is accomplished by permanently binding the heparin or heparan sulphate to a solid substrate with high surface area, and exposing it to the blood within a cartridge or filter containing this adsorption media.

The following references deal with issues discussed above:

Weber et al. (Weber V, Linsberger I, Ettenauer M, Loth F, et al. Development of specific adsorbents for human tumor necrosis factor-alpha: influence of antibody immobilization on performance and biocompatibility. *Biomacromolecules* 2005; 6: 1864-1870) reported significant in vitro binding of TNF using cellulose micro particles coated with a monoclonal anti-TNF antibody, while Haase et al. (Haase M, Bellomo R, Baldwin I, Haase-Fielitz A, et al. The effect of three different miniaturized blood purification devices on plasma cytokine concentration in an ex vivo model of endotoxinemia. *Int J Artif Organs* 2008; 31: 722-729) reported a significant reduction in IL-1ra, but not in IL-6, using a similar ex vivo methodology as ours but with a porous adsorption device. In vivo, Mariano et al. (Mariano F, Fonsato V, Lanfranco G, Pohlmeier R, et al. Tailoring high-cut-off membranes and feasible application in sepsis-associated acute renal failure: in vitro studies. *Nephrol Dial Transplant* 2005; 20: 1116-1126) are able to significantly reduce several circulating cytokines with hemoperfusion and a high cut-off polysulphone membrane, but also reported a loss of serum albumin. The putative clinical relevance of these findings are demonstrated by Schefold et al. (Schefold J C, von Haehling S, Corsepius M, Pohle C, et al. A novel selective extracorporeal intervention in sepsis: immunoadsorption of endotoxin, interleukin 6, and complement-activating product 5a. *Shock* 2007; 28: 418-425) who in a randomized study of 33 patients with septic shock are able to simultaneously reduce circulating endotoxin, IL-6, and C5a levels by selective immunoadsorption, resulting in improved organ function.

SUMMARY OF THE INVENTION

An object of the present invention is to provide a method for the removal of cytokines and/or pathogens from mammalian blood by contacting blood with a solid, essentially nonporous substrate coated with selective adsorbent molecules, biomolecules or chemical groups. Such selectively adsorbent molecules may include polysaccharides, such as heparin, heparan sulphate, polyethylene imine (PEI), sialic acid, hyaluronic acid, and carbohydrates with mannose sequences. When used prophylactically, e.g. during the collection or transfusion of banked blood, or in direct patient-to-patient transfusion of blood, the use of the present invention can also be used to lessen or eliminate the spread of disease. Thus the present invention may be used both to prevent disease, and to help cure it in previously infected patients.

One object of the invention is to provide a therapy for treating an existing disease by removing cytokines and/or pathogens from mammalian blood by contacting mammalian blood with a solid essentially nonporous substrate coated with heparin and/or other adsorbent molecules and returning the blood to the patient suffering from the disease.

The above mentioned objects are not intended to limit the scope of the invention in any way.

BRIEF DESCRIPTION OF THE DRAWINGS

FIG. 1 is a graph of TNF-α binding to heparinized beads.

DETAILED DESCRIPTION

Figure 2A:
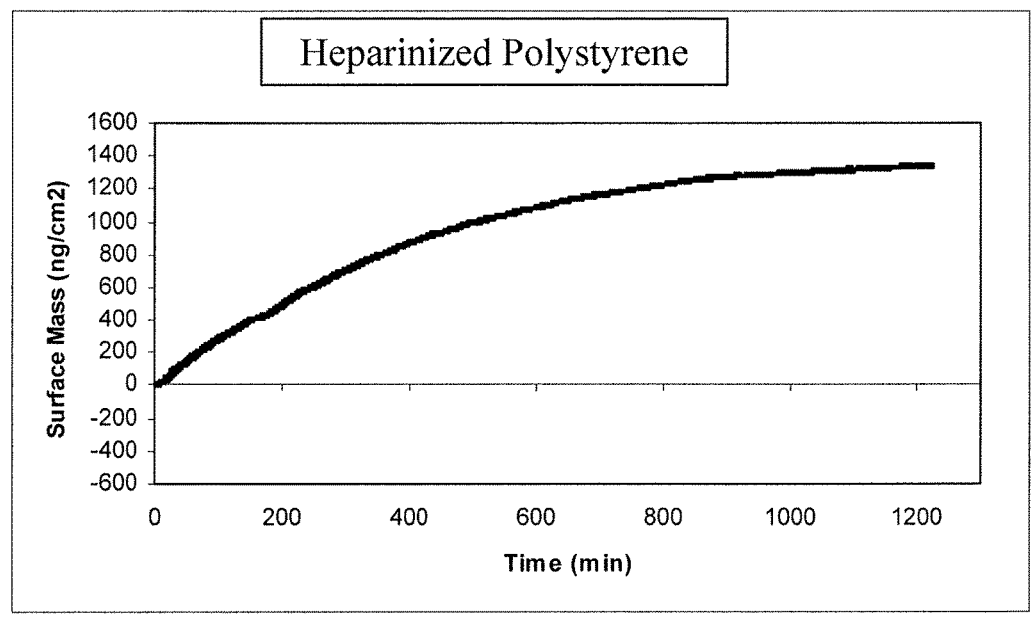
FIG. 2A is a graph of the amount of TNF-α adsorbed on the heparinized crystals.

1. Removal of Cytokines or Pathogens from the Blood

A first aspect of the present invention provides a method for the removal of cytokines and/or pathogens from blood, such as mammalian blood, by contacting the blood with a solid substrate e.g., coated with heparin and/or other adsorbent carbohydrates and/or polysaccharides.

In an embodiment of this method, heparin is immobilized onto the surface of the substrate. The inventors have found that immobilized heparin bound to a surface is effective for removing a significant amount of cytokines and pathogens from blood. However, the flow rates typical of extracorporeal blood circuits require that the adsorbent 'bed' be designed to allow relatively high flow rates to operate safely. This is in part due to the universal tendency of slow-moving or stagnant blood to form dangerous clots. In the present invention the substrate is designed with sufficiently large interstitial dimensions to permit a high flow rate of blood over the substrate without a large pressure drop. That is, as blood is taken from a mammalian patient, it is passed over the substrate at a flow rate whereby the delivery of adsorbates to the surface of the adsorbent bed is characterized primarily by forced convection. This is in contrast to the much slower process of molecular diffusion that occurs in the use of highly porous adsorbent media (e.g. porous silica, sephadex, crosslinked polystyrene and other size exclusion media), and many other microporous media. Molecular diffusion is also required when selectively-permeable barrier membranes are used together with adsorption media, e.g., to prevent contact of the adsorption media by blood cells and/or high molecular weight solutes during affinity therapy.

The binding of cytokines and pathogens by heparin and/or other adsorbent molecules during convection transport is particularly effective under the relatively high-flow conditions typically employed in the (safe) operation of extracorporeal blood circuits, e.g. when measured by linear flow velocity, ≥8 cm/min, preferably about ≥24 cm/min, and more preferably about 24-329 cm/minute, or, when measured by flow rate, around >50 mL/minute and preferably >150 mL/minute but less than about 2000 mL/minute. Adsorption within the pores of microporous media, in contrast, may require much lower flow rates through adsorption beds of practical size in order to achieve an adequate separation or purification, i.e. <50 mL/min to as low as <1 mL/min!

It is recognized that, strictly speaking, it is 'residence time' on the adsorption column that needs to be much longer for a media requiring diffusive transport of adsorbates to the adsorbent site within the media, when compared to the lower residence time needed to convey an adsorbate to the binding site (on an essentially nonporous media) by forced convection. However, there are practical limits to the dimensions of a safe and effective adsorbent cartridge, column, filter, etc., especially with respect to the maximum hold-up volume of blood it can contain, and the flow velocity of blood or serum past the adsorption media. For this reason average flow rate through the adsorption device is considered to be an important design variable.

Convection kinetics and diffusion kinetics can be compared in the removal of cytokines or pathogens from flowing blood: Adsorption media that depend on diffusion transport generally use very porous materials with extremely high internal surface area due to the presence of microscopic pores. Media suited for convection transport, on the other hand, generally rely on macroscopic "channels" or visible interstices between solid, essential nonporous material, such as particles, beads, fibers, reticulated foams, or optionally spiral-wound dense membranes.

Media that rely on forced convection transport are generally more suitable for high-flow rates, while media that rely on the much slower diffusion transport are much less effective when high flow rates and shorter residence times are required. For this reason, in an extracorporeal blood purification device, an adsorption media that does not require the adsorbate to slowly diffuse into pores within the adsorbent media is much preferred. When blood is pumped through circuits fabricated from man-made materials it is a general practice to employ relatively high blood flow rates in order to prevent stagnation and reduce the risk of clotting. On the other hand, extremely high flow rates must be avoided because they can expose blood cells to high shear rates and impingement damage that can rupture or otherwise damage blood cells. The present invention, therefore, provides a method and device for removing cytokines and/or pathogens from blood using the preferred characteristics of convection transport and its desirable, more-rapid kinetics. This is achieved by passing/flowing blood over an essentially non-microporous substrate that has been surface treated with adsorbent molecules, e.g. heparin, and which is therefore capable of binding the desired cytokine or pathogens to remove them from the blood. It is also possible to use a microporous substrate in the present invention if surface treatment renders that substrate effectively nonporous. This can occur intentionally or inadvertently, when surface treatments during media manufacturing block the pores. This converts the microporous substrate to one that does not require diffusion of adsorbate into pores to bind to the media.

The claimed methods are intended to be applied primarily in extracorporeal therapies or procedures, although implantable devices are also possible "Extracorporeal therapies" means procedures that are conducted outside the body, such as therapies in which desired products like oxygen, blood-anticoagulants, anesthetics etc can be added to body fluids. Conversely, undesired products like naturally occurring toxins or poisons can be also removed from body fluids with specific types of extracorporeal circuits. Examples are haemodialysis and haemofiltration which represent technologies whereby blood is depleted of waste products. Adsorption on activated carbon has been used to remove blood-borne poisons, and so forth.

Whole blood and blood serum from mammals can be used in the present invention. The amount of blood or blood serum that can be used in the claimed methods is not intended to be limited. It can range from less than 1 mL to above 1 L, up to and including the entire blood volume of the patient when continuous recirculation back to the patient is employed. One or more 'passes' through the adsorption bed may be used if needed. The blood may be human or animal blood.

Adsorption media to remove cytokines or pathogens from blood are optimized according to the present invention for use in traditional extracorporeal blood circulation with flow rates >50 mL/min, and preferably between about 150 and 2000 mL/min. If measured by linear flow velocity, ≥8 cm/min, preferably about ≥24 cm/min and more preferably about 24-329 cm/min. Such high flow rates create short residence times within the adsorption column and convection transport dominates over Brownian diffusive transport. This is particularly important for binding large MW proteins or cytokines such as TNF-α and larger particles such as viruses, bacteria and parasites because they diffuse very, very slowly. In the present invention the dominant adsorption sites available for removing cytokines and pathogens lie at the surfaces within the interstices of the media bed through which the blood flows or is delivered by forced convection. To treat blood, the interstitial channels need to be large enough to allow the transport of red blood cells, which are an average 6 microns in diameter. To allow a packed adsorption cartridge to be placed into an extracorporeal circuit with high blood flow rate, the interstitial channels must be several times larger than the diameter of red blood cells. This can prevent high shear rates that lead to hemolysis while simultaneously minimizing pressure drop in the blood that flows through the packed bed or cartridge. Additionally, the media is preferably rigid to minimize deformation that could clog the filter cartridge by compaction. Based on these preferences, an optimized rigid media balances interstitial channel size and total surface area, e.g., for efficient removal of pathogens and/or cytokines in high-flow extracorporeal blood circuits.

2. The Substrate Used in the Invention

Various materials, in shape and composition, can be used as a substrate in the present invention. All suitable substrates provide high surface area while promoting the conveyance of adsorbates to the adsorbent sites that bind them (primarily) by forced convective transport. The media is typically provided packed within a container, such as a column, that is designed to hold the media so that it will not be carried away in the flowing blood (a.k.a. media migration) and permit the flow of blood past essentially all of the media's surface. Useful substrates for creating the adsorption media include non-porous rigid beads, particles, or packing, reticulated foams, a rigid monolithic bed (e.g. formed from sintered beads or particles), a column packed with woven or non woven fabric, a column packed with a yarn or solid or hollow dense (not microporous) monofilament fibers, a spiral wound cartridge formed from flat film or dense membrane, or a combination of media such as a mixed bead/fabric cartridge. A suitable substrate for use in the present invention is one that is initially microporous but becomes essentially nonporous when the surface is treated before, during or after the creation of adsorption sites, e.g., via end-point-attached heparin.

The column has a macroporous structure that presents a high surface area to the blood or serum while preventing a large pressure drop and high shear rates. In addition to the potential for damaging the blood by hemolysis, high pressure drops should be avoided because they can shut down extracorporeal circuits equipped with automatic shut offs that respond to pressure drop.

The substrate may also take the form of a dense a.k.a. barrier membrane. In this embodiment, the surface of a non-porous film is modified by binding heparin, heparan sulphate or another adsorbent polysaccharide together with optional adsorbing groups not derived from heparin, heparan sulphate, or the adsorbent polysaccharide to the membrane's surface. Alternatively, a microporous membrane may be rendered nonporous or 'dense' before, during or after attachment of binding sites by filling the pores with essentially non-porous material, e.g., a polymer. The membrane in sheet or (hollow) fiber form may be arranged within a housing to present high surface area for blood contact that is suitable for use in the practice of the present invention.

2.1. Beads as Substrate

One useful substrate is in the form of solid beads or particles. The 'beads' can be made of materials that are sufficiently rigid to resist deformation/compaction under the encountered flow rates. Resistance to deformation is necessary to maintain the free volume and subsequent low pressure drop of the packed bed 'contactor'. The substantial lack of accessible pores in the bulk of the substrate eliminates the need for adsorbates to diffuse into the pores prior to adsorption. The adsorption sites of the present invention are primarily on the surface of the media and are thus positioned to be accessible to adsorbates in the blood delivered to that surface largely by convective transport. Suitable substrates need not be perfectly smooth on their surface since roughness produces a desirable increase in surface area for attachment of binding sites, e.g. by covalent or ionic bonding of heparin. Accessible internal pores with molecular dimension, on the other hand, are largely avoided to eliminate the need for adsorbates to diffuse into the pores before attaching to binding sites.

Various kinds of beads can be used in the invention. Useful beads should have sufficient size and rigidity to avoid deformation/compaction during use in the method, and have sufficient surface area to be capable of being coated with heparin for use in the method.

Evidence of sufficient substrate rigidity is the absence of a significant increase in pressure drop across the adsorption bed during about one hour of flow of water or saline at rates typical of clinical use: for example, <10-50% increase relative to the initial pressure drop (measured within the first minute of flow) when measured at similar flow rate, e.g, of saline.

The beads or other high-surface-area substrates may be made from a number of different biocompatible materials, such as natural or synthetic polymers or non-polymeric material including glasses, ceramics and metals, that are essentially free of leachable impurities. Some exemplary polymers including polyurethane, polymethylmethacrylate, polyethylene or co-polymers of ethylene and other monomers, polyethylene imine, polypropylene, and polyisobutylene. Examples of useful substrates include nonporous Ultra High Molecular Weight PolyEthylene (UHMWPE). Other suitable beads are polystyrene, high density and low density polyethylene, silica, polyurethane, and chitosan.

Methods for making such beads are per se known in the art. Polyethylene beads and other polyolefin beads are produced directly during the synthesis process and can often be used without further size reduction. Other polymers may need to be ground or spray dried and classified, or otherwise processed to create beads of the desired size distribution and shape.

As noted above, for use in the method of the invention, the size of the channels or interstitial space between individual beads for extracorporeal blood filtration should be optimized to prevent a high-pressure drop between the inlet and outlet of the cartridge, to permit safe passage of the blood cells between the individual beads in a high flow environment, and to provide appropriate interstitial surface area for binding of the polysaccharide adsorbent to the cytokines or pathogens in the blood. In a close packed bed of 300-micron, roughly spherical beads, an appropriate interstitial pore size is approximately 68 microns in diameter. Useful beads have a size ranging from about 100 to above 500 microns in diameter. The average size of the beads can be from 150 to 450 microns. For example, polyethylene beads from Polymer Technology Group (Berkeley, USA) having an average diameter of 0.3 mm are suitable. The interstitial pore is a function of bead size.

For use, the suitable beads are housed in a container, such as a column. Other suitable forms of substrate are described below.

Reticulated foams have open cells and can be made from, for example, polyurethanes and polyethylenes. Control of pore size can be achieved by controlling the manufacturing method. In general, reticulated foams can have between 3 and 100 pores/inch and can exhibit a surface area of ≥66 $cm^2/cm^3$.

Beads can be sintered into a monolithic porous structure through either chemical or physical means. Polyethylene beads can be sintered by heating the beads above their melting temperature in a cartridge and applying pressure. The resulting interstitial pore size is slightly reduced from the interstitial pore size of a packed bed of non-sintered beads of equal size. This reduction can be determined empirically and used to produce the desired final interstitial pore size.

A column or other housing shape can be packed with either woven or non-woven heparinized fabric or the heparin, heparan sulphate or optional non-heparin adsorption sites may be attached, e.g. by covalent, ionic or other chemical or physical bonds, after the housing has been filled with the substrate media. By controlling the fiber denier and density of the fabric during weaving or knitting or during the creation of a non-woven web, the interstitial pore size can be controlled. Useful non-woven fabrics may be in the form of felts, melt-blown, or electrostatically spun webs, having a random orientation held together by entanglement of the fibers and/or adhesion or cohesion of intersecting fibers. Useful woven fabrics have a more defined and non-random structure.

A column can be packed with fibers or yarns made from fibers. Polyethylene, and other fibers, can be drawn into thin hollow or solid monofilament fibers or multifilament yarns, that can be packed into cartridges in the same way that hollow fiber membranes are installed within conventional hemodialysis cartridges or blood oxygenators. In the present invention originally porous hollow fibers are rendered dense or non-porous before, during or after binding heparin or other adsorbents to the outer and/or inner surfaces. Dyneema Purity® from Royal DSM is a high-strength solid fiber made of UHMWPE. Dyneema can be heparinized and packed into a cartridge to provide a high-surface area support for the removal of cytokines and pathogens.

A spiral wound cartridge contains a thin film or membrane that is tightly wound together with optional spacer materials to prevent contact of adjacent surfaces. The membrane can be made from polymers such as polyurethane, polyethylene polypropylene, polysulfone, polycarbonate, PET, PBT, etc.

2.2. Attachment of the Adsorbant Polysaccharide

The adsorbant polysaccharide of the invention can be bound to the surface of the solid substrate by various methods, including covalent attachment or ionic attachment.

The adsorption media of the present invention can comprise heparin covalently linked to the surface of the solid substrate. Various per se known methods can be used to attach heparin to the desired substrate, such as described in a review article by Wendel and Ziemer. (H. P Wendel and G. Ziemer, European Journal of Cardio-thoracic Surgery 16 (1999) 342-350). In one embodiment, the heparin is linked to the solid substrate by covalent end-point attachment. This method increases the safety of the device by reducing or eliminating the release of heparin from the substrate surface that could enter the blood stream. 'Leaching' of heparin by and into the blood is to be avoided because it can increase the risk of bleeding and heparin-induced thrombocytopenia.

Covalent attachment of the polysaccharide, such as heparin, to a solid substrate provides better control of parameters such as surface density and orientation of the immobilized molecules as compared to non-covalent attachment. These parameters have been shown by the inventors to be important in order to provide optimal cytokine or pathogen binding to the immobilized carbohydrate molecules. The surface concentration of heparin on the solid substrate can be in the range of 1-10 µg/cm$^2$. Covalent end-point attachment means that the polysaccharide, such as heparin is covalently attached to the solid substrate via the terminal residue of the heparin molecule. Heparin can also be bound at multiple points. The end-point attachment is preferred.

If beads are used, they may be hydrophilized prior to attachment of the polysaccharide, such as heparin, or other compound. Possible methods of preparing the beads include acid etching, plasma treating, and exposure to strong oxidizers such as potassium permanganate.

2.3. Amount of Polysaccharide/Gram Substrate

The amount of polysaccharide adsorbent per gram substrate can vary. In one particular embodiment, if beads are used, the amount of polysaccharide, such as heparin per gram bead is determined by the number of layers used and also the size of the beads. The larger the bead, the less polysaccharide, such as heparin per gram of bead is achieved. One preferred amount is 2.0±0.5 mg heparin/g bead per the MBTH method.

The molecular weight of polysaccharide used in the claimed methods can vary. For example, native heparin has an average molecular weight of 22 kDa. Nitric acid degraded heparin has a molecular weight of 8 kDa.

3. Mixture of Beads with Different Surface Functionality

Heparin is a biologically active carbohydrate that can bind cytokines, pathogens, and other proteins. But heparin is best known, and most widely used as an anticoagulant that prevents blood from clotting. It has been safely used clinically for 50 years as an injectable, systemic anticoagulant. In addition, it has been used for many years by manufacturers as a coating or surface treatment for medical devices for the sole purpose of improving their safety in blood-contacting applications. This is particularly important in those devices that must expose large surface area to blood for purposes of mass transport. Examples include dialyzers and blood oxygenators. The surface of the adsorption media used in the present invention incorporates heparin for two purposes: 1) heparin's ability to bind pathogens, cytokines and other blood-borne substances that contribute to disease, and 2) heparin's ability to prevent blood coagulation and related reactions upon contact with a foreign, e.g. manmade, surface. Thus heparin is a critical component of the adsorption media of the present invention because it provide both efficacy and safety during the removal of harmful substances from blood and other biological fluids.

In addition to heparin and heparan sulfate, there are other biologically active chemical moieties including other carbohydrates that can remove harmful substances from blood and biological fluids that are not efficiently removed by immobilized heparin alone. For example, chitosan, a highly cationic, positively-charged carbohydrate will bind endotoxins. Other positively charged molecules, such as polyethylene imine (PEI), can also bind endotoxins. However, cationic surfaces are significantly less blood compatible than heparinized surfaces and can lead to increased thrombogenicity, a dangerous condition in blood contacting devices. (See Sagnella S., and Mai-Ngam K. 2005, Colloids and Surfaces B: Biointerfaces, Vol. 42, pp. 147-155, *Chitosan based surfactant polymers designed to improve blood compatibility on biomaterials* and Keuren J. F. W., Wielders S. J. H., Willems G. M., Morra M., Cahalan L., Cahalan P., and Lindhout T. 2003, Biomaterials, Vol. 24, pp. 1917-1924. *Thrombogenecity of polysaccharide-coated surfaces*). While it is possible to use an adsorption cartridge containing PEI, chitosan or other inherently throbogenic surfaces as a bioactive adsorbent to remove LPS or endotoxins from blood, due to the severe clotting risk, the patient would need a high dose of systemic anticoagulant. In the case of systemic heparin, this could lead to a bleeding risk and possible thrombocytopenia.

The method of the invention prepares the adsorption bed from a mixture of heparinized media and media which is inherently thrombogenic. By assembling an adsorption cartridge with both heparinized surfaces and, for example, cationic surfaces (or other inherently thrombogenic surfaces), cytokines, pathogens, and endotoxins can all be safely removed from blood or biological fluid.

Another biologically active, but thrombogenic carbohydrate is sialic acid. Sialic acid is known to bind virus lectins, including influenza. (C, Mandal. 1990, Experientia, Vol. 46, pp. 433-439, *Sialic acid binding Lectins*.) A mixed cartridge of heparinized beads and sialic acid coated beads can be useful in treating patients, such as during an influenza pandemic.

Abdominal septic shock is usually caused by *E. coli* which is a gram negative bacterial. Gram negative bacteria typically do not bind to heparin, and therefore it would be useful to have an adsorption column with multifunctionality to bind these bacteria in addition to cytokines and/or endotoxins. Carbohydrates with mannose sequences, such as methyl α-D-mannopyranoside, are known to bind *E. coli, K pneumonia, P. aeruginosa,* and *Salmonella.* (Ofek I., and Beachey E. H. 1, 1978, Infection and Immunity, Vol. 22, pp. 247-254, *Mannose Binding and Epithelial Cell Adherence of Escherichia coli* and Sharon, N. 2, 1987, FEBS letters, Vol. 217, pp. 145-157 *Bacterial lectins, cell-cell recognition and infectious disease.*)

The use of this embodiment is based on the concept that an antithrombogenic surface in intimate contact with, or in close proximity to a thrombogenic surface can prevent clinically significant thrombus formation that would otherwise occur if the inherently thrombogenic surface was used alone. In the case of adsorption media in the form beads or particles a preferred application of this invention is to blend the different adsorption media together before packing them into a cartridge or other housing. This provides intimate contact among the various surface chemistries on adjacent beads while permitting efficient manufacturing of adsorption cartridges or filters. A related approach is to layer the different media in a 'parfait-type' arrangement within the housing such that the blood contacts the different media in series or parallel flow. One arrangement of the different media within a cartridge is to position unblended antithrombogenic media at the entrance and/or the exit of the cartridge, with an optionally blended region containing the more thrombogenic media interposed between the entrance and exit regions. In the case of media in fiber form, a mixed woven, knitted, or nonwoven structure can be prepared by methods well known in the textile industry to form fabric from the mixed fiber. Alternatively a yarn can be prepared from finer multifilament yarn or monfilment made from two or more fibers with different surface chemistries, as long as one fiber type contains a surface that actively prevents blood clotting on contact. The mixed-fiber yarn can then be used to prepare fabric for blood contact. Hollow fiber or solid fiber adsorption media can be blended and used to make cartridges that resemble hollow-fiber dialyzers or oxygenators. For membrane or film-type adsorption media of the type that is used in a spiral-wound adsorption cartridges, two or more surface chemistries may be used in close proximity to each other such that the blood must contact both surface chemistries (nearly) simultaneously. This could be done with a regular or random array of the various binding groups within the surface layer of the membrane film, or by forming a flow path for blood between two closely-spaced membrane films, one of which is antithrobogenic.

4. Device for Use in the Methods of the Invention

Another aspect of the present invention provides use of a device comprising the adsorbent modified solid substrate, the adsorbent having a binding affinity for a cytokine or pathogen, for extracorporeal removal of the cytokine or pathogen from mammalian blood.

A device as referred to in the use and method according to the invention may comprise a conventional device for extracorporeal treatment of blood and serum from patients, e.g. suffering from renal failure.

Local blood flow patterns in blood contacting medical devices for extracorporeal circulation are known to influence clot formation via shear activation and aggregation of platelets in stagnant zones. Consequently, a device as used in the various aspects of the invention should be designed in a fashion that does not create these problems.

A device as used in some embodiments of the invention may for example have the following properties:
  A blood flow in the range of 150-2000 ml/min, or if measured by linear flow velocity of ≥8 cm/min.
  Low flow resistance.
  Large surface area of substrate having carbohydrates immobilized thereto, e.g. about 0.1-1 $m^2$.
  Stable coating (no clinically significant leakage of carbohydrate to the blood in contact therewith).
  Proper haemodynamic properties in the device (no stagnant zones).
  Optimal biocompatibility.

A non-limiting example of such a device, which can be used in a use or a method according to the present invention, is a pediatric haemoflow dialyzer which is an extracorporeal blood filtration device for removing cytokine molecules and which is compatible with high flow rates. One such device is available from Exthera Medical. Other models or types of devices for extracorporeal treatment of blood or serum may also be used, such as the Prisma M10 haemofilter/dialyzer from Gambro AB, Sweden.

High-flow conditions can be defined as blood flow above the diffusion limit.

5. Cytokines

As used herein, the term "cytokine" means a protein, released for instance in connection with microbial infection or immunization, selected from the group consisting of interleukins, interferons, chemokines and tumour necrosis factors. Examples of the cytokine(s) are vascular cell adhesion molecule (VCAM), antithrombin, Regulated on Activation Normal T Expressed and Secreted protein (RANTES), interferon, tumor necrosis factor alpha (TNF-alpha), tumor necrosis factor beta (TNF-beta), interleukin-1 (IL-1), IL-8, GRO-α and interleukin-6 (IL-6).

The method also provides for the selective removal of cytokines from the blood by strongly adsorbing heparin-binding molecules. Some molecules have a higher binding affinity for heparin than others. For example, TNF-α has a high affinity for heparin.

6. Pathogens

An additional aspect of the invention provides a method of treating a disease by removing cytokines and/or pathogens from mammalian blood by contacting mammalian blood with the solid substrate disclosed in the method above. Examples of pathogens that can be removed from the blood using heparinized substrate according to the invention include:
  Viruses—Adenovirus, Coronavirus, Dengue virus, Hepatitis B, Hepatitis C, HIV, HPV Cytomegalovirus, and others.
  Bacteria—*Bacillus anthracis, Chlamydia pneumoniaem, Listeria monocytogenes, Pseudomonas aeruginosa, Staphylococcus aureus*, MRSA, *Streptococcus pyrogenes, Yersinia enterocolitica*, and others
  Parasites—Giardia lambitia, *plasmodium* spp. and others.
  See also, Chen, Y. Gotte M., Liu J., and Park P. W., Mol. Cells, 26, 415-426.

One example of a disease to be treated according to the invention is sepsis. Sepsis is generally considered to be a systemic response to an infection which can lead to organ failure and often death. The condition can be triggered by a bacterial, viral, parasitic or fungal infection. The condition is known to be particularly dangerous in hospitals where patients may already be immuno-compromised. During sepsis, the patient experiences a so-called cytokine storm and the body's immune system attacks healthy tissue that leads to multiple organ failure in highly perfused organs. Reducing TNF-α and other inflammatory molecules will modulate the immune response and could act as an organ preservation strategy. Additionally, any heparin-binding pathogens in the blood can be removed which would help reduce further colonization and could reduce the amount of antibiotics needed to treat an infection. This could improve patient safety by reducing side effect risks associated with antibiotic therapy.

The methods of the present invention can be employed either before or after other conventional treatments, such as administration of antibiotics.

7. Combining the Inventions with Additional Filtration/Separation Steps

In an embodiment of the treatment method according to the present invention, the extraction and reintroduction of blood may be performed in a continuous loop, which loop comprises a part of the bloodstream of the subject.

In a further aspect the methods described above can be combined with other methods to filter or treat mammalian blood. For example, a cartridge that is based on convection kinetics can then be used in series with conventional extracorporeal circuits such as CPB, hemodialysis, and oxygenation.

8. Examples

The various aspects of the invention are further described in the following examples. These examples are not intended to be limiting. For instance, in the present examples heparin is used. However, other carbohydrates and polysaccharide adsorbents may be used alone or in addition to the heparin-coated substrates exemplified below.

8.1. Example 1

Preparation of Heparin Column

Polyethylene (PE) beads, with an average diameter of 0.3 mm (lot no. 180153), are supplied by the Polymer Technology Group (Berkeley, USA) and the columns (Mobicol, 1 mL) are obtained from MoBiTec (Germany). Heparin and polyethyleneimine (PEI) are purchased from Scientific Protein Laboratories (Waunakee, Wis., USA) and BASF (Ludwigshafen, Germany) respectively. All chemicals used are of analytical grade or better.

Immobilization of heparin onto the beads was performed as described by Larm et al. (Larm O, Larsson R, Olsson P. A new non-thrombogenic surface prepared by selective covalent binding of heparin via a modified reducing terminal residue. *Biomater Med Devices Artif Organs* 1983; 11: 161-173).

The polymeric surface was heparinized using the general procedure described below.

The polymeric surface is etched with a oxidizing agent (potassium permanganate, ammoniumperoxidisulfate) in order to introduce hydrophilic characteristics together with some reactive functional groups (—$SO_3H$, —OH, —C=O, —C=C—). The surface can also be etched with plasma or corona. For example, the PE-beads are etched with an oxidizing agent (potassium permanganate in sulphuric acid). These hydrophilized beads, inter alia containing OH-groups and double bonds, are later used as controls.

Reactive amino functions are introduced by treatment with a polyamine, polyethylenimine (PEI) or chitosan. For some purposes the polyamines may be stabilized on the surface by cross linking with bifunctional reagents, such as crotonaldehyde or glutaraldehyde.

The coating is further stabilized by ionic cross linking with a sulfated polysaccharide (dextran sulfate or heparin). If necessary these steps are repeated and a sandwich structure is built up. Careful rinsing (water, suitable buffers) should be performed between each step. After a last addition of PEI or chitosan, end-point attachment (EPA) to the aminated surface of native heparin is done by reductive amination, utilizing the aldehyde function in the reducing terminal residue in native heparin.

A more reactive aldehyde function in the reducing terminal residue can be achieved by partial, nitrous degradation of heparin. This shortens the reaction time, but the immobilized heparin will have a lower molecular weight. The coupling is performed in aqueous solution, by reductive amination (cyanoborohydride, $CNBH_3^-$).

In this alternate method, the aminated media is suspended in acetate buffer (800 ml, 0.1 M, pH 4.0) and 4.0 g nitrous acid degraded heparin (heparin from Pharmacia, Sweden) was added. After shaking for 0.5 h, $NaBH_3CN$ (0.4 g) was added. The reaction mixture was shaken for 24 h and then processed as above, yielding heparinized media.

1-10 µg/$cm^2$ of heparin can be coupled to all hydrophilic surfaces like glass, cellulose, chitin etc, and more or less all hydrophobic polymers like polyvinyl chloride, polyethylene, polycarbonate, polystyrene, PTFE etc.

The resulting PE-beads, with covalently end-point attached heparin, are sterilized with ethylenoxide (ETO) and rinsed with 0.9% sodium chloride and ultra pure water. The amount heparin was determined to be 2.0 mg heparin/g bead with the MBTH method. (Larm O, Larsson R, Olsson P. A new non-thrombogenic surface prepared by selective covalent binding of heparin via a modified reducing terminal residue. Biomater Med Devices Artif Organs 1983; 11: 161-173 and Riesenfeld J, Roden L. Quantitative analysis of N-sulfated, N-acetylated, and unsubstituted glucosamine amino groups in heparin and related polysaccharides. Anal Biochem 1990; 188: 383-389).

The polyethylene beads that are used had a mean diameter of 0.3 mm and are heparinized with a technology that guaranteed that the heparin molecules are covalently end point attached to the surface, thereby making the carbohydrate chains more accessible for proteins with affinity for heparin/heparan sulphate. The mean molecular weight of the immobilized heparin was about 8 kDa, while 2 mg (equal to approximately 360 IU) was coupled to each gram of beads. The integrity of this surface was verified by the expected removal of 75% of antithrombin (AT) concentrations from the blood passed over heparinized, but not non-heparinized, beads.

These data corresponds well with the previous observations from extracorporeal lung assistance (ECLA) on septic patients using surface heparinized oxygenators published by Bindslev et al. (Bindslev L, Eklund J, Norlander O, Swedenborg J, et al. Treatment of acute respiratory failure by extracorporeal carbon dioxide elimination performed with a surface heparinized artificial lung. *Anesthesiology* 1987; 67: 117-120.)

8.2. Example 2

Patients

The study protocol was approved by the local ethics committee at the Karolinska University Hospital and signed informed consent was obtained from each patient. Arterial blood was drawn from the hemodialyzers of three septic (fever >38° C., chills, leukocytes >12×$10^9$ cells/L) patients (2M/1F, aged 43, 56 and 68 years; Table 1).

TABLE 1

Clinical characteristics of patients donating blood.

| Patient | Sex | Age (years) | Body temperature (° C.) | Heart rate (beats/min) | Mean arterial pressure (mmHg) | Respiratory rate (breaths/min) | White blood cell count ($10^9$/L) |
|---|---|---|---|---|---|---|---|
| 1 | M | 43 | 39.2° | 110 | 76 | 20 | 19.0 |
| 2 | M | 56 | 38.6° | 90 | 95 | 18 | 17.5 |
| 3 | F | 68 | 38.5° | 100 | 89 | 21 | 19.5 |

The patients are previously administered with broad-spectrum antibiotics (ceftazidime or cefuroxime together with an aminoglycoside; one dose of each) and heparin (200 IU/kg body weight at the start of the dialysis). The blood was collected in EDTA vacuum tubes and immediately transferred to an adjacent room where 1 mL was applied to the previously prepared columns and passed through using a roller-pump at one of 1, 5 and 10 mL/min. Blood that had passed through the columns was immediately collected at the other end and cold-centrifuged (4500 G). The supernatants are subsequently collected and frozen at −80° C. for later analysis.

8.3. Example 3

Quantitative Analysis of Cytokines

The amounts of cytokines are determined using photoluminescence with a plate reader (Multiskan Ascent). Each sample was measured in three wells, and the geometric mean used for analysis. The intraassay coefficient of variation was below 8% for all kits. We used Coamatic antithrombin kit (Haemochrom, cat #8211991), Quantikine Human IL-6 (R&D Systems, cat #D6050), Quantikine Human IL-10 (R&D Systems, cat #D1000B), Protein C Antigen Test 96 (HL Scandinavia AB, product #H5285), Human CCL5/RANTES Quantikine (R&D Systems, cat #DRN00B), Quantikine Human sVCAM-1 (CD106) (R&D Systems, cat #DVC00), Quantikine Human IFN-gamma (R&D Systems, cat #DIF50), Quantikine HS TNF-alpha/TNFSF1A (R&D Systems, cat #HSTA00D) and BD OptEIA Human C5a ELISA Kit II (BD Biosciences, cat #557965).

Statistical Evaluation

Paired Kruskal-Wallis test was used to compare the before and after column blood concentrations of each cytokine, with a two-tailed p-value below 0.05 indicating significance. The results are summarized in Table 2.

TABLE 2

Concentrations of measured cytokines before and after blood passage through different columns.

| Cytokine | Control beads | | | Heparinized beads | |
|---|---|---|---|---|---|
| | Before passage | After passage | p-value | After passage | p-value |
| 10 g beads/1 mL blood | | | | | |
| VCAM (ng/mL) | 115.5 | 99.0 (−14%) | 0.30 | 88.8 (−23%) | <0.05 |
| IL-6 (pg/mL) | 19.7 | 17.4 (−12%) | 0.17 | 15.0 (−24%) | 0.16 |
| RANTES (pg/mL) | 147.1 | 832.5 (+466%) | <0.05 | 156.4 (+6%) | 0.61 |
| Interferon-g (pg/mL) | 340.0 | 296.0 (−13%) | 0.32 | 287.0 (−16%) | 0.45 |
| TNF-α (pg/mL) | 50.3 | 45.6 (−9%) | 0.46 | 20.6 (−59%) | <0.01 |
| Antithrombin (% activity) | 105.0 | 92.5 | 0.10 | 26.0 | <0.01 |
| 1 g beads/1 mL blood | | | | | |
| VCAM (ng/mL) | 115.5 | 99.5 (−14%) | 0.30 | 89.2 (−23%) | <0.05 |
| IL-6 (pg/mL) | 19.7 | 17.5 (−11%) | 0.17 | 15.9 (−19%) | 0.16 |
| RANTES (pg/mL) | 147.1 | 833.0 (+466%) | <0.05 | 156.8 (+7%) | 0.61 |
| Interferon-g (pg/mL) | 340.0 | 296.7 (−13%) | 0.32 | 287.5 (−15%) | 0.45 |
| TNF-α (pg/mL) | 50.3 | 46.3 (−8%) | 0.46 | 21.1 (−58%) | <0.01 |
| Antithrombin (% activity) | 105.0 | 93.0 | 0.10 | 26.8 | <0.01 |

Cytokine Binding

Pre- and post-column concentrations of analyzed cytokines are shown in Table 2 and FIG. 1. Briefly, passage through the heparinized beads resulted in a significantly bigger decrease in blood VCAM and TNF as compared to non-heparinized beads.

Impact of Bead Volume

Data obtained with a 1:1 and 1:10 blood-to-bead volume did not vary significantly (Table 2).

Impact of Flow Rate

Varying the blood flow rate from 1 up to 10 mL/min did not significantly affect the amount removed of the respective cytokines, indicating that the observed binding to the immobilized heparin molecules is a very rapid event and is clearly not dependent on diffusion kinetics.

8.4. Example 4

In this example, 5 liters of platelet poor plasma in which recombinant TNF-α had been added was tested with a clinically sized cartridge. A 300 ml cartridge was packed with heparinized PE beads as described in Example 1. The device was sterilized using ETO sterilization using the 16 hour cycle with a temperature of 50 degrees. The device was allowed to "gas out" for an additional 12 hours prior to the start of the study.

5.1 L of frozen, unfiltered porcine heparinized platelet poor plasma from Innovative Research was purchased, and stored in a −20 degree freezer until the day of use. 1 mg of Recombinant Human Tumor Necrosis Factor-α was received from Invitrogen in powder form.

The morning of the procedure the plasma was removed from the −20 degree C. freezer and placed into a warm water bath to thaw. 1 ml sterile water was mixed with the 1 mg powdered TNF-α to reconstitute to a concentration of 1 mg/ml.

A Fresenius 2008K dialysis machine was set up with a "Combiset" hemodyalisis blood tubing (standard tubing used on the Fresenius machine) in a closed system set up with the seraph hemofilter in place of the Fresenius Kidney. 5 L of plasma was transferred into a 5 L reservoir bag which was connected to the arterial and venous patient lines. The dialysis machine along with tubing was primed with saline to ensure proper function and that there was no air through the closed circuit.

The 5 L bag of plasma was placed on a plate rocker with a Bair Hugger warming blanket wrapped around to maintain temperature throughout the procedure. At this point the pre-infusion control sample was collected and placed in liquid nitrogen for snap freezing. The sample was then moved to a sample storage box and placed on dry ice. After all connections were confirmed, 0.415 ml TNF-α was injected into the port of the reservoir bag. The plasma with TNF-α was allowed to mix on the rocker for 10 minutes before the post-infusion control sample was collected. The post-infusion sample was collected, snap frozen in liquid nitrogen, then moved to the sample box on dry ice. The dialysis system was purged of saline and the system clock was started when the plasma was passed through the closed system. The first sample was collected upstream from the filter at 5 minutes.

For the 1$^{st}$ hour of the test run, samples were collected every 5 minutes from the port immediately upstream and also immediately downstream from the Hemofilter. The samples were snap frozen in liquid nitrogen and placed in the sample storage box on dry ice.

For the 2$^{nd}$ and 3$^{rd}$ hour of the test run the samples were collected every 10 minutes from the port immediately upstream and immediately downstream from the hemofilter. The samples were snap frozen in liquid nitrogen and placed in the sample storage box on dry ice.

For the 4$^{th}$ and 5$^{th}$ hour of the test run, samples were collected every 20 minutes from both the upstream and downstream ports. These samples were also snap frozen in liquid nitrogen, and placed in the sample storage box on dry ice.

At each sample collection, both upstream and downstream for each time point, a new needle and a new syringe was used to avoid residual TNF-α.

ELISAs were performed to monitor the amount of TNF-α in the plasma. To coat the 96-well plates, 10 μL of the capture antibody was diluted in 10 μL of coating buffer A and 100 μL was added to each well. The plate was covered with parafilm and stored at 4° C. overnight or over the weekend. Samples were removed from the –80° C. freezer, logged, and allowed to thaw. Plates were removed from the 4° C. refrigerator and wells aspirated, washed once with 400 μL/well of Assay buffer, then inverted and blotted on absorbent paper towels. 300 μL of Assay buffer were added to each well and the plates were incubated for 60 minutes. During this time, standards were prepared from the TNF-α standard included with the CytoSet by dilution in Assay buffer. Thawed samples were diluted in assay buffer. Once samples were diluted, they were replaced in the proper places in the freezer boxes and returned to the –80° C. freezer, as indicated by the log. Plates were washed again with 400 μL/well of Assay buffer, inverted, and blotted. The 100 μL was placed in the wells according to the ELISA template sheets. Samples and standards were run in duplicate and a standard curve was included on each plate. 8.8 μL of detection antibody was diluted in 5.49 mL Assay buffer and 50 μL was added to each well as soon as all samples and standards were added. Plates were incubated for 2 hours at room temperature on an orbital shaker. Plates were washed and aspirated 5 times as described above. The streptavidin conjugate (16 μL) was diluted in 10 mL of Assay buffer and 100 mL was added to each well. Plates were incubated 30 minutes at room temperature on the orbital shaker then washed with Assay buffer 5 times as described above. 100 μL of the TMB solution was added to each well and plates were incubated a further 30 minutes on the orbital shaker. 100 μL of the stop solution was added to each well and the plate was read at 450 nm on a Vmax plate reader within 30 minutes of adding the stop solution.

The results of the test are plotted in FIG. 1. Within 40 minutes of continuous cycling of TNF rich serum, an 80% reduction of TNF was observed, with no subsequent release. With ideal mixing, all of the TNF in the plasma would have passed over the adsorption column in 33 minutes. Removal of TNF-α through adsorption based on convection kinetics is demonstrated as the majority of TNF was captured in this time period.

8.5. Example 5

A quartz crystal microbalance (QCM) experiment was performed to attempt to normalize the uncompetitive binding capacity of TNF-α to a heparinized surface. QCM is a technique that can detect the weight of adsorbents on specially prepared crystals. The minimum detection limit is 0.5 ng/cm$^2$. QCM detects the resonance frequency of the crystal. As the mass of the crystal increases through adsorption, the resonance frequency changes in proportion to the gain in mass. The change in mass (Δm) is described in the following equation $$\Delta m = -C \frac{1}{n} \Delta f \quad \begin{matrix} C = 17.7 \text{ ngcm}^{-2}\text{s}^{-1} \\ n\text{-overtone} \end{matrix}$$

where Δf is the change in frequency.

Figure 2B:
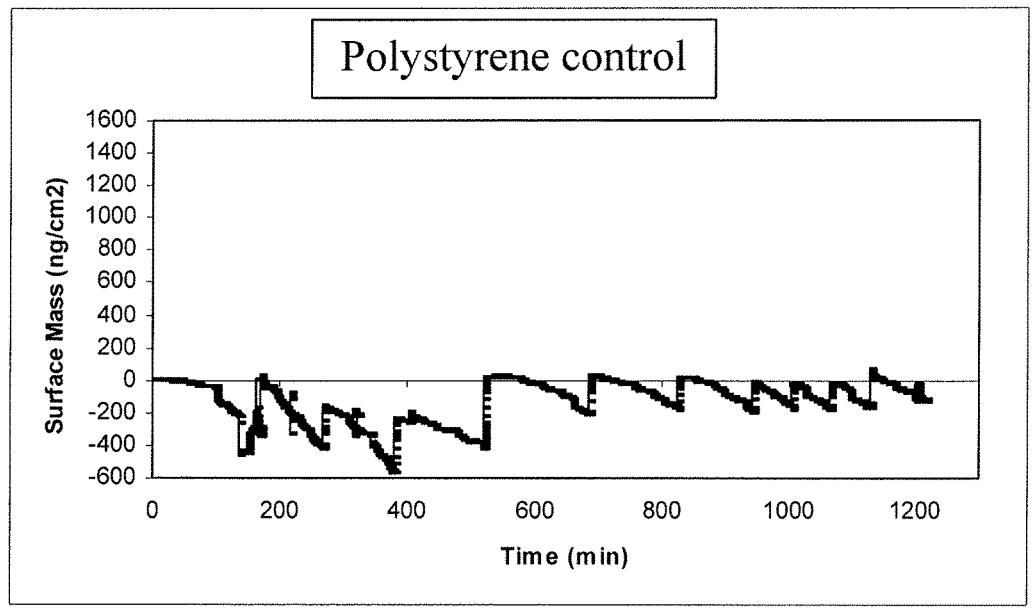
FIG. 2B is a graph of the amount of TNF-α adsorbed onto control crystals.

Polystyrene coated QCM crystals were heparinized following the method described in example 1. A 120 ml solution was prepared where recombinant TNF-α was added to PBS for a final concentration of 83 μg/L. The solution was then flowed through a cell containing 4 QCM crystals at a rate of 50 μl/min. Two crystals were heparinized and two were control crystals (untreated polystyrene). The total time of the experiment was 20 hours. The results for the amount of TNF-α adsorbed on the heparinized crystals and the controls are shown in FIG. 2. A maximum of 1234 ng/cm$^2$ of TNF-α adsorbed on the heparinized crystal and a adsorption on the control surfaces was negligible.

8.6. Example 6

A study was performed testing the removal of cytokines from plasma sampled from *Bacillus anthracis* infected macaques using heparinized beads. The plasma was collected at the time of death of several animals and pooled. 1 ml filter syringes were packed with either 0.5 grams of PE beads heparinized following the procedure outlined in Example 1 or untreated PE beads for use as controls. A total of three sample syringes and three control syringes were used. A top porous plate was placed on top of the beads to keep the beads from floating as saline or plasma was added to the filter syringes. The filter syringes were primed using 2 ml of Tris-buffered Saline (TBS). The 2 ml of saline was passed through the filter syringe using a 5 ml syringe. The plunger of the 5 ml syringe was then retracted and filled with 4 ml of air. The air was then passed through the filter syringe to force the remaining saline out of the beads. 0.5 ml of plasma was then pulled into the 5 ml syringe and then pressed through the filter syringe. An additional 4 ml of air was passed through the filter syringe to remove any residual plasma. After the plasma drained through the syringe, aliquots were sampled and flash froze for cytokine concentration analysis. A Luminex® Multiplex assay was used to test for GRO-α, IL-8, MIP-1β, Rantes, and TNF-β. The results are summarized in Table 3.

TABLE 3

| Cytokine | Before Passage Levels (pg/ml) | Passage Through Control Beads (pg/ml) | % Removed Control | Passage Through Heparin Beads (pg/ml) | % Removed Heparin Beads |
|---|---|---|---|---|---|
| GRO-α | 263.5 | 158.5 | 39.8% | 77.66 | 70.6% |
| IL-8 | 504.9 | 460.8 | 8.7% | 312.4 | 38.1% |
| MIP-1β | 66.2 | 56.4 | 14.8% | 51.8 | 21.8% |

TABLE 3-continued

| Cytokine | Before Passage Levels (pg/ml) | Passage Through Control Beads (pg/ml) | % Removed Control | Passage Through Heparin Beads (pg/ml) | % Removed Heparin Beads |
|---|---|---|---|---|---|
| RANTES | 1105.3 | 930.3 | 15.8% | 559.7 | 49.4% |
| TNF-β | 7.3 | 7.9 | −8.2% | 4.3 | 41.4% |

8.7. Example 7

Cartridge to Bind Cytokines and Endotoxins Using a Layered Assembly

A cartridge is built using two different adsorption media. Heparinized beads are used to capture cytokines and PEI beads are used to capture endotoxins. By controlling the ratio of heparinized to PEI beads, blood compatibility can be maintained. The PEI beads are made following the first two steps in Example 1.

In this example, a cartridge is built with heparinized beads and polyethyleneimine (PEI) coated beads. A 300 ml adsorption column is fixed to a vertical stand. 50 ml of 300 micron average heparinized beads are then added to the cartridge and allowed to settle. A 50:50 mixture of PEI and heparinized beads is then added and makes up the next 200 ml. The cartridge is then filled to the top with a final 50 ml of heparinized beads. The cartridge is then sealed and the close packing of the beads maintain the layered structure of the adsorption media. In this cartridge, $\frac{2}{3}^{rds}$ of the beads are heparinized while $\frac{1}{3}^{rd}$ is aminated and therefore inherently thrombogenic.

8.8. Example 8

Cartridge to Bind Cytokines and Endotoxins Using a Uniform Mixture of Beads

A cartridge is built using two different adsorption media. Heparinized beads are used to capture cytokines and PEI beads are used to capture endotoxins. By controlling the ratio of heparinized to PEI beads, the overall blood compatibility of the device can be maintained.

In this example, a cartridge is built with heparinized beads and PEI coated beads. A 300 ml adsorption column is fixed to a vertical stand. 100 ml of PEI coated beads are added to 200 ml of heparinized beads and mixed thoroughly. The 300 ml of beads are then added to the cartridge and sealed. The close packing of the beads maintains the random mixture of beads. In this cartridge, $\frac{2}{3}^{rds}$ of the beads are heparinized while $\frac{1}{3}^{rd}$ are aminated.

8.9. Example 9

Cartridge to Bind Cytokines, Gram Negative Bacteria, and Endotoxins Using a Layered Assembly A cartridge is built using three different adsorption media. Heparinized beads are used to capture cytokines, mannose functionalized beads are used to capture gram negative bacteria, and PEI beads are used to capture endotoxins. By controlling the ratio of heparinized beads, mannose functionalized beads, and PEI coated beads, blood compatibility can be maintained.

A 300 ml adsorption column is fixed to a vertical stand. 50 ml of 300 micron average heparinized beads are then added to the cartridge and allowed to settle. 200 ml of beads, with equal quantities of heparinized beads, PEI beads, and mannose functionalized beads are then added to the cartridge. The cartridge is then filled to the top with a final 50 ml of heparnized beads. The cartridge is then sealed and the close packing of the beads maintain the layered structure of the adsorption media. In this cartridge, 55.6% of the beads are heparinized, 22.2% are PEI beads, and 22.2% are mannose functionalized.

The embodiments of the present invention are further described in the claims below.

What is claimed is:

1. A device for removing an adsorbate selected from cytokines, pathogens and toxins from blood, the device comprising: a container which comprises a solid substrate of high surface area having at least one polysaccharide adsorbent on the surface thereof with a binding affinity for the adsorbate, wherein the at least one polysaccharide comprises a carbohydrate with mannose sequences; and wherein the solid substrate has interstitial channel spaces large enough to permit the transport of blood cells, and during blood flow the adsorbate binds to binding sites on the at least one polysaccharide adsorbent becoming separated from the blood and the transport of the adsorbates from blood to adsorbent sites on the solid substrate is primarily by convection transport.

2. The device of claim 1, wherein the solid substrate is a member selected from the group consisting of beads, fibers, reticulated foams, and spiral-wound dense membranes.

3. The device of claim 2, wherein the solid substrate is comprises a plurality of rigid polymer beads.

4. The device of claim 3, wherein the rigid polymer beads are rigid polyethylene beads.

5. The device of claim 4, wherein the beads have a diameter ranging from 100 to 450 microns.

6. The device of claim 5, wherein the beads have an average diameter of 0.3 mm.

7. The device of claim 1, wherein the at least one polysaccharide further comprises a member selected from the group consisting of heparin, heparan sulfate, hyaluronic acid, sialic acid, and chitosan.

8. The device of claim 2, wherein the beads are coated with 0.5-10 mg heparin per gram of bead.

9. The device of claim 8, wherein the heparin has a mean molecular weight of about 8 kDa.

10. The device of claim 8, wherein the heparin is attached to the substrate by covalent end-point attachment.

11. The device of claim 1, wherein the at least one polysaccharide with mannose sequences is end-point attached.

12. The device of claim 10, wherein the container further comprises a solid substrate having on the surface thereof a cationic, positively charged molecule having an affinity for the cytokine, pathogen or toxin, but being more thrombogenic than heparin.

13. The device of claim 12, wherein the cationic, positively charged molecule is chitosan or polyethylene imine.

14. A method for removing an adsorbate selected from cytokines, pathogens and toxins from blood, the method comprising:

contacting blood with a device having a solid substrate of high surface area with at least one polysaccharide adsorbent on the surface thereof with a binding affinity for the adsorbate, wherein the at least one polysaccharide adsorbent comprises a carbohydrate with mannose sequences; and wherein the solid substrate has interstitial channel spaces large enough to permit the transport of blood cells, and during blood flow the adsorbate binds to binding sites on the at least one polysaccharide adsorbent, becoming separated from the blood and wherein the transport of the adsorbates from blood to adsorbent sites on the solid substrate is primarily by convection transport, to thereby remove the adsorbate.

15. The method of claim 14, wherein the solid substrate is a member selected from the group consisting of beads, fibers, reticulated foams, and spiral-wound dense membranes.

16. The method of claim 15, wherein the solid substrate comprises a plurality of rigid polymer beads.

17. The method of claim 14, wherein the linear flow velocity of blood flowing through the device is between about 8 and 24 cm/minute.

18. The method of claim 14, wherein the at least one polysaccharide with mannose sequences is end-point attached.

19. The method of claim 14, wherein the device further comprises a solid substrate having on the surface thereof a cationic, positively charged molecule having an affinity for the cytokine, pathogen or toxin, but being more thrombogenic than heparin.

20. The method to claim 14, wherein the cytokine is selected from the group consisting of IL-6, VCAM, TNF-α, GRO-α, IL-8, and RANTES.

* * * * *